United States Patent [19]

Mac Laury

[11] 4,228,308
[45] Oct. 14, 1980

[54] DEHYDROCHLORINATION OF A DIHYDROXYDIPHENYL TRICHLOROETHANE

[75] Inventor: Michael R. Mac Laury, Rexford, N.Y.

[73] Assignee: General Electric Company, Schenectady, N.Y.

[21] Appl. No.: 37,436

[22] Filed: May 9, 1979

[51] Int. Cl.³ .................................. C07C 39/367
[52] U.S. Cl. .......................... 568/726; 568/725; 568/774
[58] Field of Search ................ 568/726, 774, 725

[56] References Cited

U.S. PATENT DOCUMENTS

| | | | |
|---|---|---|---|
| 3,686,337 | 8/1972 | Chang | 568/774 |
| 4,097,538 | 6/1978 | Factor et al. | 568/726 |
| 4,117,018 | 9/1978 | Cleveland et al. | 568/726 |

*Primary Examiner*—Werren B. Lone
*Attorney, Agent, or Firm*—Joseph T. Cohen; James C. Davis, Jr.

[57] ABSTRACT

1,1,1-trichloro-2,2-bis(4-hydroxyphenyl)ethane can be dehydrohalogenated to 1,1-dichloro-2,2-bis(4-hydroxyphenyl) ethylene by treating the former with a dehydrochlorinating agent comprising liquid methyl amine and an effective amount of an additive to accelerate the dehydrochlorinating effect of the liquid methyl amine selected from the class consisting of a certain class of inorganic and organic salts.

6 Claims, No Drawings

DEHYDROCHLORINATION OF A DIHYDROXYDIPHENYL TRICHLOROETHANE

This invention is concerned with a process for dehydrohalogenating a dihydroxydiphenyl trichloroethane. More particularly, the invention is concerned with a process for obtaining in good yield and purity, and at an accelerated rate, the compound 1,1-dichloro-2,2-bis(4-hydroxyphenyl)ethylene (hereinafter referred to as "dichloride") having the formula

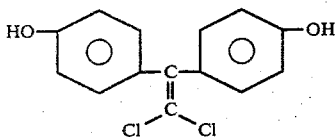

by treating 1,1,1-trichloro-2,2-bis(4-hydroxyphenyl)ethane (hereinafter referred to as "trichloride") having the formula

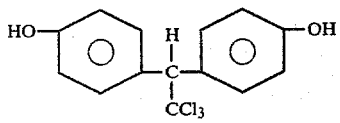

with liquid methyl amine in the presence of an effective amount of an additive selected from the class consisting of certain organic and inorganic salts.

In my copending application Ser. No. 4050 filed Jan. 17, 1979, and assigned to the same assignee as the present invention, is disclosed a process for dehydrohalogenating the aforesaid trichloride to the dichloride by employing liquid methyl amine as the dehydrohalogenating agent. As pointed out in the aforesaid application, the rate of dehydrohalogenation is considerably faster than when using ammonia as a dehydrohalogenating agent as more particularly disclosed and claimed in U.S. Pat. No. 4,097,538—Factor et al, issued June 27, 1978. Although the methyl amine operates at a faster rate of dehydrohalogenation than the ammonia, it has been found that slightly more impurities are obtained, particularly compounds of the formulas

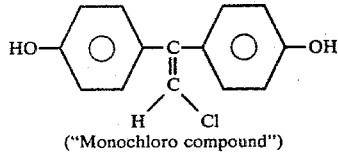
("Monochloro compound")

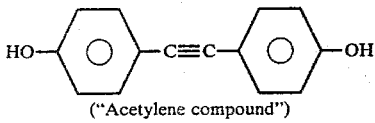
("Acetylene compound")

However, the disadvantages of the formation of somewhat larger amounts of these impurities is more than offset by the fact that the methyl amine operates at a much faster rate than the ammonia in dehydrochlorinating the trichloride, and in addition the methyl amine effects such dehydrohalogenation at lower temperatures and pressures than is normally practicable with liquid ammonia.

I have now unexpectedly discovered that I can still further accelerate the rate of dehydrochlorination of the liquid methyl amine of the trichloride to the dichloride and obtain a dichloride containing somewhat less of the impurities than when using the liquid methyl amine above, if with the liquid methyl amine I employ a certain class of organic and inorganic salts selected from the class consisting of methyl amine hydrochloride and hydrobromide, ethyl amine hydrochloride and hydrobromide, dimethyl amine hydrochloride and hydrobromide, ammonium chloride and bromide, lithium chloride and bromide, and sodium chloride and bromide. The presence of these salts does not affect the advantage of being able to use the liquid methyl amine at lower temperatures and pressures than are employed with liquid ammonia. What is even more unexpected and significant is the fact that under essentially comparable conditions, the half life ($T_{\frac{1}{2}}$) using the liquid methyl amine with the salts is about 25% less than when liquid methyl amine is used without the salts, and the percent of unreacted trichloride remaining after reaction with the methyl amine containing the salts is significantly lower.

In accordance with my invention, I have unexpectedly discovered that effective amounts of the salts of the class described above, when added to the methyl amine significantly increased the rate of dehydrohalogenation while retaining the advantage of the methyl amine in attaining a good purity of material and good yield. The purified dichloride thus obtained after isolation needs little if any further purifiction and can be used to make flame-resistant, flame-retardant resins by treatment of the dichloride of formula I with either diphenyl carbonate or phosgene to form polycarbonate resins.

It was entirely unexpected and in no way could have been predicted that the aforementioned class of salts would be able to accelerate the dehydrohalogenating action of the liquid methyl amine. For example, under essentially equivalent conditions, it was found that the methyl amine hydrochloride greatly increased the rate of dehydrohalogenation despite the fact that in the reaction between the methyl amine and the trichloride, methyl amine hydrochloride is produced.

The presence of small amounts of the salt with the liquid methyl amine does not interfere with the advantages inherent in the use of the methyl amine itself. In the first place, no additional solvent of any kind is required since the liquid methyl amine acts as both the reactant and the solvent medium. In order to separate the dichloride from the reaction solution, one only needs to allow the methyl amine to evaporate from the reactor and remove any salt by suitable means. Moreover, the dichloride obtained by this procedure after the by-products and salt additives are removed (advantageously using a methanol-water medium or water washes) is free of usual impurities in products obtained by previous procedures at a similar stage of purification, for instance, by treating the trichloride with a large molar excess of aqueous sodium hydroxide at elevated temperatures [see M. Trojna and H. Hubacek, Chem. Listy 51, 752 (1957)]. If further purification of the dichloride by crystallization from methanol-water (whose pH has been adjusted to between 3 to 7) is used, the product obtained is as good if not better both in color and in freedom from impurities than products obtained by prior art procedures.

Although a large molar excess of methyl amine is used to serve both as the reactant and the solvent medium, the dehydrochlorination only uses 1 mol of the methyl amine per mol of trichloride, and at the end of the reaction the unused methyl amine can be easily recovered by evaporation or distillation. Generally, on a molar ratio from 2 to 20 mols of methyl amine are used per mol of the trichloride.

The amount of the salt used in combination with the liquid methyl amine can be varied widely and only requires an amount of the former effective to induce the accelerated dehydrohalogenation action of the liquid methyl amine. Based on the liquid methyl amine employed, one can use from 0.5 to 20% or more, by weight, of the salt based on the weight of the methyl amine. Stated alternatively, the salt can be used in amounts ranging from about 1 to 15 or more mol percent of the salt based on the molar concentration of the liquid methyl amine.

In accordance with my invention, the dehydrochlorination of the trichloride can be achieved by charging the trichloride to a pressure reactor together with the liquid methyl amine and the salt, and thereafter heating the pressure reactor at temperatures ranging from 35° to 125° C., and preferably from 50° to 100° C., for times ranging from about 10 minutes to 6 hours or more to effect dehydrohalogenation. Thereafter, the formed dichloride can be removed from the liquid methyl amine-salt mixture, by first allowing the methyl amine to volatilize and collecting the latter, and then dissolving the remaining solid material in aqueous methanol and crystallizing the dichloride from that solution by adding water in which the dichloride is insoluble. If further purification is desired, the dichloride can be recrystallized in the manner described above with a methanol-water mixture. It is evident that the size of the pressure reactor used will in many instances dictate the molar concentrations of the methyl amine, the salt, and the trichloride undergoing dehydrohalogenation.

Depending on the temperatures and the amount of methyl amine and salt present in the reactor, pressures ranging from 50 psi to 700–800 psi or more can be employed without materially affecting the results. Again, the temperatures used will depend on the type and size of the pressure reactor employed, the molar concentrations of the methyl amine, the salt, the trichloride, etc. Because the reaction using the salt with the methyl amine can be run at somewhat lower temperatues than when methyl amine is used alone without any significant increase in impurities, total reaction times of shorter duration are possible than with other methods for dehydrohalogenation. Thus, it has been found that at any reasonable temperature of reaction (50° to 100° C.) the combination of the methyl amine and the salt will cause completion of the dehydrohalogenation reaction in a significantly shorter time than when the methyl amine is used alone.

Under the pressure conditions employed in the practice of my invention, temperature, of course is an important function in the attainment of a substantially pure dichloride. Thus, as one proceeds from around room temperature (about 20°–30° C.) to about 125° C., one will find that with the use of reasonable times of reaction, for instance, about 30–90 minutes at the upper end of the temperature range, essentially all of the trichloride is converted to the dichloride in a fairly pure state.

Although the reaction between the methyl amine and the trichloride can be carried out without any additional ingredients, the use of non-reactive solvents is not precluded. Included among such solvents may be mentioned methanol, dimethyl formamide, N-methyl pyrrolidone, N,N-dimethylacetamide, dimethyl sulfoxide, etc. Amounts of such solvents, for instance, by weight, from about 0.1 to 2 parts of the solvent per part of the trichloride, can be used to advantage in some instances in order to reduce the amount of excess liquid methyl amine which may be required.

In order that those skilled in the art may better understand how the present invention may be practiced, the following examples are given by way of illustration and not by way of limitation. In some instances, the amounts of ingredients used in the reaction are recited both on a weight and mol percent basis.

EXAMPLE 1

About 0.6 gram (0.00189 mol) of the trichloride of formula II were dissolved in about 10 ml (7.0 grams, 0.225 mol) methyl amine condensed at −78° C. in a pressure reaction vessel. The reaction vessel was immersed in a constant temperature bath closed and heated at 50° C. for 15 minutes while the mixture inside the pressure vessel was continuously agitated. The pressure vessel was opened and the excess liquid methyl amine allowed to evaporate; final removal of the methyl amine was accomplished by the use of vacuum. The solid product was dissolved in 80% aqueous methanol (5% solids), acidified to a pH of 3–5 with concentrated HCl, and diluted with water to form a 50% aqueous methanol solution. This solution was heated to about 75° to 80° C. and then slowly cooled to room temperature (about 25° C.) and then analyzed to determine the degree of dehydrochlorination and the amount of unreacted trichloride still present in the reaction mixture.

EXAMPLE 2

The same procedure and proportions of ingredients were used as in Example 1 for effecting the reaction between methyl amine and trichloride but in this example, ammonium chloride was added in one instance and methyl amine hydrochloride added in another instance. The reactants were heated and stirred similarly as in Example 1 and the products isolated and the reaction mixtures analyzed.

The following Table I shows the effect of using ammonium chloride and methyl amine hydrochloride with the methyl amine and the half life in minutes ($T_{1/2}$) for the reactions described in Examples 1 and 2. The mol percents and weight percents of the salts recited were based on the methyl amine used.

TABLE I

| Salt | Weight Percent | Mol Percent | [1]Mol Percent Trichloride | [2]$T_{\frac{1}{2}}$ (minutes) |
| --- | --- | --- | --- | --- |
| None | — | — | 42.6 | 12 |
| NH$_4$Cl | 14.7 | 8.6 | 30.6 | 9 |
| CH$_3$NH$_2$ . HCl | 18.6 | 8.6 | 30.5 | 9 |

[1]After 15 minutes at 50° C.
[2]Half life of reaction.

EXAMPLE 3

When methyl amine hydrobromide, ethyl amine hydrochloride, ethyl amine hydrobromide, dimethyl amine hydrochloride, dimethyl amine hydrobromide, ammonium bromide, lithium chloride, lithium bromide, sodium chloride, and sodium bromide are used in essentially the same amounts and under the same conditions as described in Example 2, it will be found that these salts exert an accelerating dehalogenating effect when the methyl amine is used as a dehydrohalogenation agent similarly as in the aforesaid Example 2.

It will be evident from the above examples that the use of small amounts of the salts in combination with the liquid methyl amine permits faster rates of reaction without any decrease in the advantage of using methyl amine alone. As a matter of fact, it has been found that the color of the final dichlorides when using the salts with the methyl amine was lighter than when the methyl amine was used alone.

The dichloride obtained in accordance with the present invention has many uses. One of the more important uses to which this composition may be put is as an intermediate in the preparation of heat-resistant polyester resins. For instance, the dichloride can be reacted with phthalic acid esters or certain phthalic acids themselves, such as dimethyl terephthalate, terephthalic acid, isophthalic acid, etc., to make polyester resins. An important use for the dichloride is in the preparation of flame and heat resistant polycarbonate resins by reacting the dichloride with precursor carbonating agents, such as phosgene, diphenyl carbonate, etc.

The polymeric compositions derived from the reaction of the dichloride here desribed have many applications. These polymeric compositions may be used to form fibers, films, or molded products. Thus, either by extrusion from melt or by depositing from solution, fibers derived from these polymeric compositions may be formed and used in the preparation of various textile materials designed for clothing and similar applications.

Various fillers may be incorporated in the polymeric compositions prior to molding thereof. Among such fillers may be mentioned glass fibers, carbon black, titanium dioxide, silica, mica, bentonite, etc. Molded products derived from such a mixture of ingredients can be used as gears, handles for cooking utensils, etc. The incorporation of abrasive particles such as carborundum, diamond powder, etc., makes molded products derived from such polymeric compositions useful as grinding wheels, etc. The addition of carbon, silicon carbide, powdered metal, conducting oxides, etc., to the polymeric compositions results in the so-called resistance or semiconducting paints which have many useful applications.

It will of course be understood by those skilled in the art that in addition to the conditions, ingredients, and concentrations of ingredients described in the foregoing examples, other conditions, ingredients, and concentrations, examples of which are discussed previously, may be used without departing from the scope of the invention. It is intended to include within the scope of the claims herein appended any changes or modifications which may be indicated as advantageous in the practice of the invention.

What I claim as new and desire to secure by Letters Patent of the United States is:

1. In a process for dehydrohalogenating the trichloride, 1,1,1-trichloro-2,2-bis-(4-hydroxyphenyl) ethane, to form the dichloride of the formula

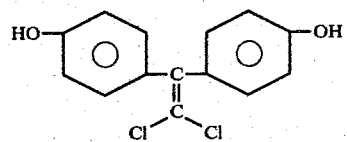

which process comprises (1) treating the aforesaid trichloride with liquid methyl amine in an amount sufficient to act as both a dehydrohalogenating agent and solvent, the improvement comprising the said methyl amine in combination with an amount of a salt effective to accelerate the dehydrohalogenation reaction, wherein said salt is selected from the class consisting of methyl amine hydrochloride and hydrobromide, ethyl amine hydrochloride and hydrobromide, dimethyl amine hydrochloride and hydrobromide, ammonium chloride and bromide, lithium chloride and bromide, and sodium chloride and bromide, to form a substantially pure dichloride of the above formula, and (2) removing the unreacted methyl amine and salt thereby isolating the desired dichloride, the said salt being used in an amount ranging from 0.5 to 20%, by weight, based on the weight of the methyl amine.

2. The process as in claim 1 wherein the salt comprises from 0.5 to 20%, by weight, based on the weight of the methyl amine.

3. The process as in claim 1 wherein there is present a molar ratio of from 2 to 20 mols liquid methyl amine per mol trichloride.

4. The process as in claim 1 wherein the salt is $NH_4Br$.

5. The process as in claim 1 wherein the salt is $CH_3NH_2.HCl$.

6. In a process for dehydrohalogenating the trichloride, 1,1,1-trichloro-2,2-bis(4-hydroxyphenyl) ethane, to form the dichloride of the formula

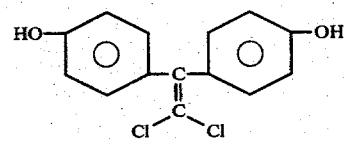

which process comprises (1) treating the aforesaid trichloroethane with liquid methyl amine in an amount sufficient to act as both dehydrohalogenating agent and solvent, the improvement comprising the said methyl amine in combination with an amount of $NH_4Cl$ effective to accelerate the dehydrohalogenation reaction, and (2) removing the unreacted methyl amine and ammonium chloride to yield the above-described dichloride, the $NH_4Cl$ being used in an amount ranging from 0.5 to 20%, by weight, based on the weight of the methyl amine.

* * * * *